(12) United States Patent
Von Raven et al.

(10) Patent No.: US 10,883,715 B2
(45) Date of Patent: Jan. 5, 2021

(54) POWER-GENERATION SYSTEM HAVING A COMBINED HEAT AND POWER PLANT AND METHOD FOR POWER GENERATION

(71) Applicant: Martin GmbH fuer Umwelt-und Energietechnik, Munich (DE)

(72) Inventors: Robert Von Raven, Seeshaupt (DE); Ulrich Martin, Munich (DE); Max Josef Schoensteiner, Neutraubling (DE)

(73) Assignee: Martin GmbH fuer Umwelt- und Energietechnik, Munich (DE)

( * ) Notice: Subject to any disclaimer, the term of this patent is extended or adjusted under 35 U.S.C. 154(b) by 129 days.

(21) Appl. No.: 16/055,306

(22) Filed: Aug. 6, 2018

(65) Prior Publication Data
US 2019/0049111 A1 Feb. 14, 2019

(30) Foreign Application Priority Data
Aug. 10, 2017 (DE) .......... 10 2017 007 547

(51) Int. Cl.
*F23G 5/44* (2006.01)
*C12M 1/107* (2006.01)
(Continued)

(52) U.S. Cl.
CPC ........... *F23G 5/442* (2013.01); *C07C 1/12* (2013.01); *C07C 9/04* (2013.01); *C12M 21/04* (2013.01); *C12M 21/16* (2013.01); *C12M 43/08* (2013.01); *C25B 1/04* (2013.01); *F01K 13/00* (2013.01); *F23G 5/02* (2013.01); *C10L 3/08* (2013.01); *C10L 2290/02* (2013.01); *C10L 2290/06* (2013.01); *C10L 2290/26* (2013.01);
(Continued)

(58) Field of Classification Search
CPC ........... C07C 1/12; Y02E 20/12; C21M 21/16
See application file for complete search history.

(56) References Cited

U.S. PATENT DOCUMENTS

| 9,057,138 B2 | 6/2015 | Stuermer et al. |
| 2007/0217995 A1* | 9/2007 | Matsumura ............... C25B 1/04 423/657 |

(Continued)

FOREIGN PATENT DOCUMENTS

| DE | 196 21 751 C1 | 11/1997 |
| DE | 10 2007 060 666 A1 | 6/2009 |

(Continued)

OTHER PUBLICATIONS

German Search Report in DE 10 2017 007 547.6, dated Jun. 27, 2018, with English translation of relevant parts.
(Continued)

*Primary Examiner* — Nicholas A Smith
(74) *Attorney, Agent, or Firm* — Collard & Roe, P.C.

(57) ABSTRACT

A power-generation system having a combined heat and power plant and a fermentation plant has an electrolysis plant, which is connected by lines to both the combined heat and power plant and to the fermentation plant. This arrangement enables a method in which heat from a combined heat and power plant can be used for a fermentation plant and additionally heat from an electrolysis plant can be used for the fermentation plant, whilst the oxygen from the electrolysis plant is used for the combined heat and power plant.

13 Claims, 1 Drawing Sheet

(51) Int. Cl.
  *C25B 1/04* (2006.01)
  *F01K 13/00* (2006.01)
  *C12M 1/00* (2006.01)
  *C12M 1/16* (2006.01)
  *C07C 1/12* (2006.01)
  *C07C 9/04* (2006.01)
  *F23G 5/02* (2006.01)
  *C10L 3/08* (2006.01)

(52) U.S. Cl.
  CPC ...... *C10L 2290/38* (2013.01); *F23G 2200/00* (2013.01); *F23G 2206/20* (2013.01); *F23G 2206/203* (2013.01); *F23G 2900/50208* (2013.01); *Y02E 20/12* (2013.01)

(56) References Cited

U.S. PATENT DOCUMENTS

2011/0245572 A1* 10/2011 Wolf .................. C12M 47/18
                                                      585/800
2016/0285266 A1*  9/2016 Rüdlinger ............ C10J 3/62
2017/0218404 A1*  8/2017 Simpson .............. C12M 43/00

FOREIGN PATENT DOCUMENTS

| DE | 10 2009 007 567 A1 | 9/2009 | |
|----|----|----|----|
| DE | 10 2009 018 126 A1 | 10/2010 | |
| DE | 102009036005 A1 * | 2/2011 | ............ C25B 1/04 |
| DE | 102010017818 A1 * | 8/2011 | ............ C07C 31/04 |
| DE | 202013103888 U1 * | 9/2013 | ............ C05B 7/00 |
| DE | 102012204985 A1 * | 10/2013 | ............ C25B 15/08 |
| EP | 1 634 946 A1 | 3/2006 | |
| WO | 2010/115983 A1 | 10/2010 | |
| WO | 2015/120983 A1 | 8/2015 | |

OTHER PUBLICATIONS

European Search Report in EP 18000536.5 dated Nov. 26, 2018 with an English translation of relevant parts.

* cited by examiner

POWER-GENERATION SYSTEM HAVING A COMBINED HEAT AND POWER PLANT AND METHOD FOR POWER GENERATION

CROSS REFERENCE TO RELATED APPLICATIONS

Applicant claims priority under 35 U.S.C. § 119 of German Application No. 10 2017 007 547.6 filed Aug. 10, 2017, the disclosure of which is incorporated by reference.

BACKGROUND OF THE INVENTION

1. Field of the Invention

The invention relates to a power-generation system having a combined heat and power plant and a fermentation plant, which are connected to one another by means of a line, in order to use heat from the combined heat and power plant for the fermentation plant.

2. Description of the Related Art

Plants of this type are very advantageous, as above all waste heat with a low energy level is particularly suitable for use in a fermentation plant.

SUMMARY OF THE INVENTION

The invention is based on the object of developing a power-generation system of this type. This object is achieved using a power-generation system with the features according to one aspect of the invention. A method for power generation with the features according to another aspect of the invention shows an advantageous procedure for using the resultant power particularly well.

Advantageous developments are discussed below.

According to the invention, the power-generation system has an electrolysis plant, which is connected by means of lines to both the combined heat and power plant and to the fermentation plant. This makes it possible to improve the efficiency of the power-generation system.

If the combined heat and power plant is a waste incineration plant, a part of the waste can be treated in the fermentation plant, whilst another part is incinerated.

In practice, it has been established that it is advantageous if the fermentation plant is a plant for dry fermentation.

An advantageous embodiment provides that the combined heat and power plant and the fermentation plant are also connected to one another directly by means of a power line, in order to use power generated at the combined heat and power plant for the fermentation plant. That is to say that part of the power generated using the heater is not fed into a public power grid, but rather is used directly for operating the fermentation plant.

It is particularly advantageous if the electrolysis plant and the fermentation plant are connected to one another heat by means of a line for heat, in order to use heat generated during the electrolysis for the fermentation plant.

In addition, the electrolysis plant and the fermentation plant may be connected to one another by means of a line for gas, in order to use hydrogen produced during the electrolysis for the fermentation plant. In this case, the hydrogen can be used in the fermentation to increase methane production, in that hydrogen is already supplied during fermentation.

Alternatively or cumulatively, it may be provided that the electrolysis plant and the fermentation plant are connected to one another by means of a line for gas, in order to mix hydrogen, produced during the electrolysis, with gas, produced during fermentation. Gas refinement is achieved as a result.

Power generated at the combined heat and power plant may be used not only for the fermentation, but also for the electrolysis. Therefore, it is suggested that the electrolysis plant and the combined heat and power plant are connected to one another directly by means of a power line, in order to use power generated at the combined heat and power plant for the electrolysis plant. The power is therefore not initially introduced into a public power grid in order to be used from there for the electrolysis, rather a direct line between the combined heat and power plant and electrolysis plant enables the use of power generated at the combined heat and power plant for the electrolysis.

Accordingly, the electrolysis plant and the combined heat and power plant can also be connected to one another by means of a line, in order to use steam or heat produced at the combined heat and power plant for the electrolysis plant. The line may therefore be a steam or hot-water line for example.

It is advantageous if the electrolysis plant and the combined heat and power plant are connected to one another by means of a line for gas, in order to use oxygen produced during the electrolysis for the combined heat and power plant.

The individual plants, in which the gas, which should be used in a different plant, accumulates, naturally have a certain gas storage device, in which the gas accumulates. In order to control the gas exchange between the components of the power-generation system and/or to provide the gas for third parties, it is suggested that the power-generation system has a gas storage device which has a volume of more than 50 $m^3$.

A particular development of the power-generation system provides that the power-generation system has a methane-gas production plant, which is connected to the combined heat and power plant and/or the fermentation plant by means of lines for carbon dioxide and to the electrolysis plant by means of a line for hydrogen. This makes it possible to integrate a methane-gas production plant into the power-generation system in a particularly advantageous manner.

It is advantageous in this case if the methane-gas production plant is connected to the combined heat and power plant and/or to the electrolysis plant by means of a line for heat. As a result, even internally generated heat can be used for the methane-gas production plant.

Accordingly, internally generated power can also be used for the methane-gas production plant if the methane-gas production plant is connected to the combined heat and power plant directly by means of a power line, in order to use power generated at the combined heat and power plant for the methane-gas production plant.

Accordingly, a method for power generation provides using heat from a combined heat and power plant for a fermentation plant and additionally using heat from an electrolysis plant for the fermentation plant, wherein the oxygen from the electrolysis is used for the combined heat and power plant. This method is suitable for a power-production system according to the invention in particular.

In this case, it is advantageous if hydrogen from the electrolysis plant is converted to methane using carbon dioxide from dry fermentation.

In order to supply gas, produced during the method, for further use, it is suggested that at least one gas flow created in the power-generation system is stored. This gas flow may be carbon dioxide, hydrogen, oxygen, methane and/or biogas. This makes it possible to control the gas production and the gas consumption in the individual components of the plant more easily, as the storage devices allow a temporal coupling, at least to a limited extent.

BRIEF DESCRIPTION OF THE DRAWINGS

Advantageous exemplary embodiments are illustrated in the drawing and are explained in more detail in the following. In the figures.

DETAILED DESCRIPTION OF PREFERRED EMBODIMENTS

Figure 1:
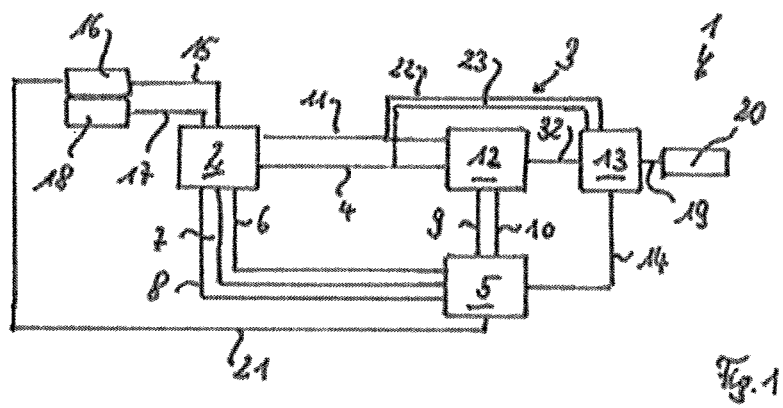
FIG. 1 shows a power-generation system with combined heat and power plant, fermentation plant and electrolysis plant.

The power-generation system 1 created in FIG. 1 has a waste incineration plant as combined heat and power plant 2. This waste incineration plant delivers power for the fermentation plant 3 which is constructed as a dry fermentation plant. A line 4 is arranged between the combined heat and power plant 2 and the fermentation plant 3 for this purpose, so that heat from the combined heat and power plant 2 can be used for the fermentation plant 3.

Furthermore, the power-generation system 1 has an electrolysis plant 5, which is connected by means of lines 6 to 10 both to the combined heat and power plant 2 and to the fermentation plant 3.

A power line 11 connects the combined heat and power plant 2 to the fermentation plant 3 directly, in order to use power generated at the combined heat and power plant 2 for the fermentation plant 3.

The electrolysis plant 5 and the fermentation plant 3 are connected to one another by means of a line 9 for heat and by means of a line 10 for gas, in order to use heat generated during the electrolysis and hydrogen produced during the electrolysis for the fermentation plant 3. The fermentation plant 3 has a plant for dry fermentation 12 and a gas refinement plant 13. This makes it possible also to mix hydrogen produced during the electrolysis in the fermentation plant 3 in the gas refinement plant 13 by means of a line 14 between the electrolysis plant 5 and the fermentation plant 3.

The electrolysis plant and the combined heat and power plant 2 can be connected to one another by means of a line 6, in order to use steam or heat produced at the combined heat and power plant 2 for the electrolysis plant 5. A power line 7 between electrolysis plant 5 and combined heat and power plant 2 makes it possible to use power generated at the combined heat and power plant 2 for the electrolysis plant directly and a line 8 for gas between the electrolysis plant 5 and the combined heat and power plant 2 makes it possible to use oxygen produced during the electrolysis for the combined heat and power plant 2.

This power-generation system 1 is connected to a power grid 16 by means of a power line 15. A line 17 connects the power-generation system 1 to a heating grid 18 and a line 19 connects the fermentation plant 3 to a gas supply 20. This makes it possible, by means of the line 15, to discharge heat via the line 17 and gas via the line 19 from the power-generation system.

A line 21 makes it possible additionally to supply the electrolysis plant 5 with power from the power grid 16. In addition, the gas refinement plant 13 can be supplied with power from the combined heat and power plant 2 via a power line 22 and with heat from the combined heat and power plant 2 via a line 23.

Figure 2:
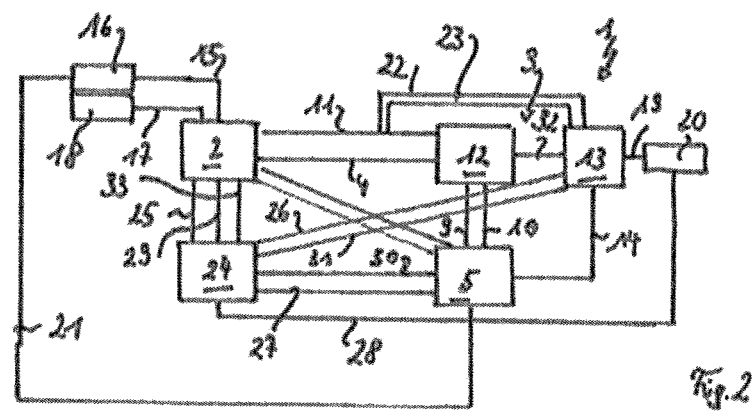
FIG. 2 shows a power-generation system according to FIG. 1 having a methane-gas production plant.

FIG. 2 shows the integration of a methane-gas production plant 24 into the power-generation system 1 shown in FIG. 1. In this case, all components are provided with identical reference numbers. The methane-gas production plant 24 is constructed as a P2G (power to gas) plant and receives $CO_2$ by means of the line 25 from the combined heat and power plant 2 and $CO_2$ from the gas refinement plant 13 of the fermentation plant 3 by means of the line 26. Using hydrogen supplied by means of the line 27 from the electrolysis plant 5, the methane-gas production plant produces methane which is supplied to the gas supply 20 by means of the line 28. A line 29 provides the methane-gas production plant 24 with heat from the combined heat and power plant 2 and a line 30 provides the methane-gas production plant 24 with heat from the electrolysis plant 5.

The gas produced in the methane-gas production plant 24 can either be supplied to the gas supply directly by means of the line 28 or initially supplied to the gas refinement plant 13 by means of a line 31. This gas refinement plant 13 receives biomethane gas by means of the line 32 from the dry fermentation plant 12 with integrated gas treatment.

The line 33 is used as a power line supplying the methane-gas production plant 24 with power from the combined heat and power plant 2.

The combination of combined heat and power plant 2, dry fermentation plant 12 and electrolysis plant 5 makes it possible to supply the dry fermentation plant 12 and the electrolysis plant 5 with power from the combined heat and power plant. The electrolysis plant 5 consequently improves the efficiency of the combined heat and power plant 2 and the dry fermentation plant 12 and it increases the calorific value of the gas produced in the fermentation plant 3. In addition, the electrolysis decouples the circuit from the power grid as a current sink.

The further integration of the methane-gas production plant 24 uses this plant as a $CO_2$ sink and enables use of the biogenic $CO_2$ produced in the dry fermentation plant 12 (carbon capture, negative $CO_2$ balance). In addition, the methane-gas production plant enables further decoupling from the power grid as a hydrogen sink.

Figure 3:
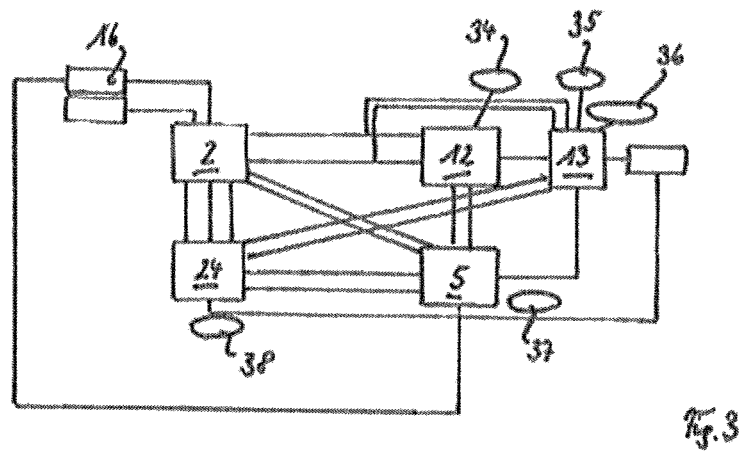
FIG. 3 shows a power-generation system according to FIG. 2 having gas storage devices.

FIG. 3 shows how the dry fermentation plant 12 is connected to a storage device 34 for biogas and the gas refinement plant 13 is connected to storage devices 35 for $CO_2$ and 36 for biomethane gas. The electrolysis plant 5 is connected to a storage device 37 for hydrogen and the methane-gas production plant 24 is connected to a storage device 38 for methane gas. This storage device primarily enable a strengthened decoupling from the power grid 16.

Although only a few embodiments of the present invention have been shown and described, it is to be understood that many changes and modifications may be made thereunto without departing from the spirit and scope of the invention.

What is claimed is:

1. A power-generation system having a combined heat and power plant and a fermentation plant,
wherein the power-generation system has an electrolysis plant, which is connected via lines to both the combined heat and power plant and to the fermentation plant, wherein the combined heat and power plant is a waste incineration plant, wherein the fermentation plant has a plant for dry fermentation, wherein the combined heat and power plant and the fermentation plant are directly connected with each other via a first power line in order to use power generated by the combined heat and power plant for the fermentation plant, wherein the electrolysis plant and the fermentation plant are connected with each other via a line for heat in order to use heat generated during electrolysis for the fermentation plant, or wherein a line is arranged between the combined heat and power plant and the fermentation plant in order that heat generated by the combined heat and power plant can be used for the fermentation plant, and wherein the electrolysis plant and the combined heat and power plant are directly connected to one another via a second power line in order to use the power generated by the combined heat and power plant for the electrolysis plant.

2. The power-generation system according to claim 1, wherein the electrolysis plant and the fermentation plant are connected to one another via a line for gas, in order to use hydrogen produced during the electrolysis for the fermentation plant.

3. The power-generation system according to claim 1, wherein the electrolysis plant and the fermentation plant are connected to one another via a line for gas, in order to mix hydrogen, produced during the electrolysis, with gas, produced in the fermentation plant, in a gas-refinement plant.

4. The power-generation system according to claim 1, wherein the electrolysis plant and the combined heat and power plant are connected to one another via a line, in order to use steam or heat produced at the combined heat and power plant for the electrolysis plant.

5. The power-generation system according to claim 1, wherein the electrolysis plant and the combined heat and power plant are connected to one another via a line for gas, in order to use oxygen produced during the electrolysis for the combined heat and power plant.

6. The power-generation system according to claim 1, wherein the power-generation system has at least one gas storage device which has a volume of more than 50 $m^3$.

7. The power-generation system according to claim 1, wherein the power-generation system has a methane-gas production plant, which is connected to the combined heat and power plant and/or the fermentation plant via lines for carbon dioxide and to the electrolysis plant via a line for hydrogen.

8. The power-generation system according to claim 7, wherein the methane-gas production plant is connected to the combined heat and power plant and/or to the electrolysis plant via a line for heat.

9. The power-generation system according to claim 7, wherein the methane-gas production plant is directly connected to the combined heat and power plant via a power line, in order to use power generated at the combined heat and power plant for the methane-gas production plant.

10. A method for power generation using the system according to claim 1, in which heat of the combined heat and power plant is delivered to the fermentation plant, wherein heat of the electrolysis plant is additionally delivered to the fermentation plant and the oxygen from the electrolysis plant is delivered to the combined heat and power plant.

11. The method according to claim 10, wherein hydrogen of the electrolysis plant is converted to methane using carbon dioxide from the fermentation.

12. The method according to claim 10, wherein at least one gas flow produced in the power-generation system is stored.

13. The method according to claim 10, wherein gas which is produced and stored is supplied for further use in a controlled manner.

* * * * *